(12) United States Patent
Uhrich et al.

(10) Patent No.: US 8,741,317 B2
(45) Date of Patent: Jun. 3, 2014

(54) SLOW-DEGRADING POLYMERS COMPRISING SALICYLIC ACID FOR UNDELAYED AND SUSTAINED DRUG DELIVERY

(75) Inventors: Kathryn E. Uhrich, New Brunswick, NJ (US); Roselin Rosario-Meléndez, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/213,843

(22) Filed: Aug. 19, 2011

(65) Prior Publication Data

US 2012/0058155 A1    Mar. 8, 2012

Related U.S. Application Data

(60) Provisional application No. 61/375,216, filed on Aug. 19, 2010.

(51) Int. Cl.
| | |
|---|---|
| A61K 9/00 | (2006.01) |
| A61K 31/765 | (2006.01) |
| C08G 63/181 | (2006.01) |
| A61K 31/185 | (2006.01) |
| C08G 67/04 | (2006.01) |

(52) U.S. Cl.
CPC .............. *A61K 31/185* (2013.01); *C08G 67/04* (2013.01)
USPC .......... 424/400; 424/78.37; 428/402; 528/194

(58) Field of Classification Search
CPC ............................... A61K 31/775; C08G 67/04
USPC ................ 424/400, 78.37; 428/402; 528/194
See application file for complete search history.

(56) References Cited

U.S. PATENT DOCUMENTS

| | | |
|---|---|---|
| 2,607,799 A | 8/1952 | Weesner |
| 4,062,855 A | 12/1977 | Allan et al. |
| 4,126,445 A | 11/1978 | Allan et al. |
| 4,164,560 A | 8/1979 | Folkman et al. |
| 4,298,595 A | 11/1981 | Parkinson et al. |
| 4,591,496 A | 5/1986 | Cohen et al. |
| 4,684,620 A | 8/1987 | Hruby et al. |
| 4,757,128 A | 7/1988 | Domb et al. |
| 4,792,598 A | 12/1988 | Ziegast |
| 4,857,311 A | 8/1989 | Domb et al. |
| 4,868,274 A | 9/1989 | Gupta et al. |
| 4,886,870 A | 12/1989 | D'Amore et al. |
| 4,888,176 A | 12/1989 | Langer et al. |
| 4,891,225 A | 1/1990 | Langer et al. |
| 4,906,474 A | 3/1990 | Langer et al. |
| 4,916,204 A | 4/1990 | Domb et al. |
| 4,938,949 A | 7/1990 | Borch et al. |
| 4,997,904 A | 3/1991 | Domb |
| 4,999,417 A | 3/1991 | Domb |
| 5,032,216 A | 7/1991 | Felten |
| 5,082,925 A | 1/1992 | Shalaby et al. |
| 5,160,745 A | 11/1992 | DeLuca et al. |
| 5,175,235 A | 12/1992 | Domb et al. |
| 5,259,968 A | 11/1993 | Emert et al. |
| 5,264,540 A | 11/1993 | Cooper et al. |
| 5,290,494 A | 3/1994 | Coombes et al. |
| 5,317,079 A | 5/1994 | Domb et al. |
| 5,364,725 A | 11/1994 | Wilson et al. |
| 5,498,729 A | 3/1996 | Domb |
| 5,512,131 A | 4/1996 | Kumar et al. |
| 5,514,764 A | 5/1996 | Frechet et al. |
| 5,518,730 A | 5/1996 | Fuisz |
| 5,545,409 A | 8/1996 | Laurencin et al. |
| 5,629,009 A | 5/1997 | Laurencin et al. |
| 5,660,851 A | 8/1997 | Domb |
| 5,721,131 A | 2/1998 | Rudolph et al. |
| 5,776,748 A | 7/1998 | Singhvi et al. |
| 5,798,115 A | 8/1998 | Santerre et al. |
| 5,837,278 A | 11/1998 | Geistlich et al. |
| 5,891,477 A | 4/1999 | Lanza et al. |
| 5,902,110 A | 5/1999 | Alfano et al. |
| 5,902,599 A | 5/1999 | Anseth et al. |
| 5,916,585 A | 6/1999 | Cook et al. |
| 5,937,758 A | 8/1999 | Maracas et al. |
| 5,942,252 A | 8/1999 | Tice et al. |
| 5,958,911 A | 9/1999 | Evans et al. |
| 5,969,020 A | 10/1999 | Shalaby et al. |
| 6,071,530 A | 6/2000 | Polson et al. |
| 6,123,956 A | 9/2000 | Baker et al. |

| R= | Polymer |
|---|---|
| (CH₂)₄ | 1a (SA-adipic) |
| CH₂OCH₂ | 1b (SA-diglycolic) |
| | 1c (SA-DEM) |

| | | | |
|---|---|---|---|
| 6,153,212 A | 11/2000 | Mao et al. | |
| 6,171,610 B1 | 1/2001 | Vacanti et al. | |
| 6,280,772 B1 | 8/2001 | Pinkus | |
| 6,365,149 B2 | 4/2002 | Vyakarnam et al. | |
| 6,468,519 B1 | 10/2002 | Uhrich | |
| 6,486,214 B1 | 11/2002 | Uhrich | |
| 6,602,915 B2 | 8/2003 | Uhrich | |
| 6,613,807 B2 | 9/2003 | Uhrich | |
| 6,685,928 B2 | 2/2004 | Uhrich et al. | |
| 6,689,350 B2 | 2/2004 | Uhrich | |
| 7,122,615 B1 | 10/2006 | Uhrich | |
| 7,396,527 B2 | 7/2008 | Uhrich | |
| 7,411,031 B2 | 8/2008 | Uhrich et al. | |
| 7,534,852 B2 | 5/2009 | Uhrich | |
| 7,662,864 B2 | 2/2010 | Kanamathareddy et al. | |
| 7,666,398 B2 | 2/2010 | Uhrich | |
| 7,901,705 B2 | 3/2011 | Roby et al. | |
| 7,985,415 B2 | 7/2011 | Giroux | |
| 8,017,714 B2 | 9/2011 | Uhrich | |
| 8,088,405 B2 | 1/2012 | Uhrich | |
| 8,221,790 B2 | 7/2012 | Uhrich | |
| 8,232,322 B2 | 7/2012 | East | |
| 8,241,668 B2 | 8/2012 | Uhrich | |
| 8,263,060 B2 | 9/2012 | Uhrich | |
| 8,361,453 B2 | 1/2013 | Uhrich et al. | |
| 2001/0046476 A1 | 11/2001 | Plochocka | |
| 2004/0038948 A1 | 2/2004 | Uhrich | |
| 2004/0096476 A1 | 5/2004 | Uhrich et al. | |
| 2005/0249697 A1 | 11/2005 | Uhrich et al. | |
| 2006/0013851 A1 | 1/2006 | Giroux | |
| 2006/0057179 A1 | 3/2006 | Giroux | |
| 2007/0098800 A1 | 5/2007 | Giroux et al. | |
| 2007/0196417 A1 | 8/2007 | Uhrich | |
| 2010/0272670 A1 | 10/2010 | Uhrich et al. | |
| 2010/0291180 A1 | 11/2010 | Uhrich | |
| 2010/0291181 A1 | 11/2010 | Uhrich et al. | |
| 2010/0310498 A1 | 12/2010 | Kanamathareddy et al. | |
| 2013/0022569 A1 | 1/2013 | Uhrich et al. | |

FOREIGN PATENT DOCUMENTS

| | | |
|---|---|---|
| AU | 750424 | 3/2003 |
| CA | 2393676 | 7/2002 |
| DE | 288311 | 3/1991 |
| DE | 0288387 | 3/1991 |
| EP | 0246341 | 11/1987 |
| EP | 0498283 | 8/1992 |
| EP | 0580386 | 1/1994 |
| FR | 2839451 | 11/2003 |
| JP | 45-004740 | 2/1970 |
| JP | 51-134729 | 11/1976 |
| JP | 53-082743 | 7/1978 |
| JP | 56-007716 | 1/1981 |
| JP | 6255797 | 12/1985 |
| JP | 61186309 | 8/1986 |
| JP | 06-328857 | 11/1994 |
| JP | 07-149044 | 6/1995 |
| NL | 9000237 | 8/1991 |
| WO | WO 90/09779 | 9/1990 |
| WO | WO 91/09831 | 7/1991 |
| WO | WO 97/39738 | 10/1997 |
| WO | WO 97/44016 | 11/1997 |
| WO | WO 97/49385 | 12/1997 |
| WO | WO 98/36013 | 8/1998 |
| WO | WO 99/12990 | 3/1999 |
| WO | WO 99/29885 | 6/1999 |
| WO | WO 99/36107 | 7/1999 |
| WO | WO 00/66730 | 11/2000 |
| WO | WO 01/28492 | 4/2001 |
| WO | WO 01/41753 | 6/2001 |
| WO | WO 02/09767 | 2/2002 |
| WO | WO 02/09768 | 2/2002 |
| WO | WO 02/09769 | 2/2002 |
| WO | WO 03/046034 | 6/2003 |
| WO | WO 03/065928 | 8/2003 |
| WO | WO 03/066053 | 8/2003 |
| WO | WO 03/072020 | 9/2003 |
| WO | WO 2004/006863 | 1/2004 |
| WO | WO 2004/039355 | 5/2004 |
| WO | WO 2004/045549 | 6/2004 |
| WO | WO 2005/039489 | 5/2005 |
| WO | WO 2005/042600 | 5/2005 |
| WO | WO 2006/127667 | 11/2006 |
| WO | WO 2007/143698 | 12/2007 |
| WO | WO 2008/034019 | 3/2008 |
| WO | WO 2008/103744 | 8/2008 |
| WO | WO 2008/128193 | 10/2008 |
| WO | WO 2009/026544 | 2/2009 |

OTHER PUBLICATIONS

Prudencio et al. (Effect of the Linker Structure on Salicylic Acid-Derived Poly(Anhydride-Esters), Macromolecules (2005) 38, 6895-6901), 7 pages.*

Aebischer, P., et al., "Basic fibroblast growth factor released from synthetic guidance channels facilitates peripheral nerve regeneration across long nerve gaps", *Journal of Neuroscience Research*, 23(3), 282-289, (Jul. 1989).

Amann et al., "Anti-inflammatory effects of aspirin and sodium salicylate", *European Journal of Pharmacology*, 447, 1-9 (2002).

Anastasiou, T.J., "Novel, Degradable Polyanhydrides", *25th Annual Meeting Transactions of the Society for Biomaterials*, Abstract, 79, (1999).

Anastasiou, T.J., "Novel Polyanhydrides with Enhanced Thermal and Solubility Properties", *Macromolecules*, 33(17), 6217-6221, (2000).

Anastasiou, T.J., "Synthesis of Novel, Degradable Polyanhydrides Containing Para-Aminosalicylic Acid as Drug Delivery Devices for Tuberculosis Treatment", *Polymer Preprints*, 41(2), 1366-1367, (Aug. 2000).

Attawia, M.A., "Biocompatibility Testing of Poly(anhydride-co-imides) Containing Pyromellitylimidoalanine", *The 21st Annual Meeting of the Society for Biomaterials*, Abstract, 222, (Apr. 5-9, 1994).

Attawia, M.A., "Cytotoxicity testing ofpoly(anhydride-co-imides) for orthopedic applications", *Journal of Biomedical Materials Research*, 29(10), 1233-1240, (1995).

Attawia, M.A., "In vitro bone biocompatibility of poly(anhydride-co-imides) containing pyromellitylimidoalanine", *Journal of Orthopedic Research*, 14(3), 445-454, (1996).

Attawia, M.A., "The Long Term Osteoblast Response to Poly(anhydride-co-imides): A New Degradable Polymer for Use in Bone", *Proceedings of the Fifth World Biomaterials Congress*, Toronto, Canada, 113, (1996).

Attawia, M.A., "Proliferation, Morphology, and Protein Expression by Osteoblasts Cultured on Poly(anhydride-co-amides)", *Journal of Biomedical Materials Research*, 48(3), 322-327, (1999).

Attawia, M.A., "Regional drug delivery with radiation for the treatment of Ewing's sarcoma—in vitro development of a taxol release system", *Journal of Controlled Release*, 71, 193-202 (2001).

Beaton, M.L., "Synthesis of a novel poly(anhydride-ester)", *The Rutgers Scholar—An Electronic Bulletin of Undergraduate Research*, 3, 1-7, (2001), http://www.scils.rutgers.edu/~weyang/ejournal/volume03/beatuhri/beatuhri.htm.

Bedell, C., "Processing and Hydrolytic Degradation of Aromatic, Ortho-Substituted Polyanhydrides", *Journal of Applied Polymer Science*, 80, 32-38, (2001).

Brambley, D., et al., "Microlithography: an overview", *Advanced Materials for Optics and Electronics*, 4(2), 55-74, (Mar.-Apr. 1994).

Branch, D.W., "Microstamp patterns of biomolecules for high resolution neuronal networks", *Medical & Biological Engineering & Computing*, 36(1), 135-41, (Jan. 1998).

Brown, J.P., "A Polymeric Drug for Treatment of Inflammatory Bowel Disease", *Journal of Medicinal Chemistry*, 26(9), 1300-1307, (1983).

Brown, L., et al., "Transderrnal delivery of drugs", *Annual Review of Medicine*, 39, 221-9, (1988).

Campo, C.J., "Polyanhydrides: the effects of ring substitution changes on polymer properties", *Polymer Bulletin*, 42, 61-68, (1999).

Carbone et al., "Design and Synthesis of Fast-Degrading Poly(anhydride-esters)", *Macromol. Rapid Commun.*, 30, 1021-1026 (2009).

Chafi, N., "Dosage Form with Salicylic Acid Attached to the Polyanhydride Polymer Dispersed in an Eudragit Matrix", *International Journal of Pharmaceutics*, 52, 203-211, (1989).

Chatterjee, R., et al., "Mechanism for the Increase in Solubility of Deoxyhemoglobin S due to Cross-Linking the Beta Chains Between Lysine-82 Beta1 and Lysine-82 Beta 2", *Biochemistry*, 21, 5901-5909, (1982).

Chen, G., "Effect of protein and cell behavior on pattern-grafted thermoresponsive polymer", *Journal of Biomedical Materials Research*, 42(1), 38-44, (Oct. 1998).

Conix, A., "New High-Melting Fibre-Forming Polymers", *Die Makromolekulare Chemie*, XXIV, 76-78, (1957).

Conix, A., "Aromatic Polyanhydrides, a New Class of High Melting Fiber-Forming Polymers", *Journal of Polymers Science*, XXIX, 343-353, (1958).

Conix, A., "Poly [1,3-bis (p carboxyphenoxy)—Propane anhydride]", *Macromolecular Synthesis*, 2, 95-99, (1996).

Davaran, S., "Release of 5-amino Salicylic Acid from Acrylic Type Polymeric Prodrugs Designed for Colon-specific Drug Delivery", *Journal of Controlled Release*, 58(3), 279-287, (1999).

Davies, M.C., "The Analysis of the Surface Chemical Structure of Biomedical Aliphatic Polyanhydrides Using SPX and ToF-SIMS", *Journal of Applied Polymer Science*, 42, No. 6, New York, US, 1597-1605, (Mar. 20, 1991).

Delamarche, E., et al., "Patterned delivery of immunoglobulins to surfaces using microfluidic networks", *Science*, 276(5313), 779-781, (May 2, 1997).

Dewez, J.L., et al., "Adhesion of mammalian cells to polymer surfaces: from physical chemistry of surfaces to selective adhesion on defined patterns", *Biomaterials*, 19(16), 1441-1445, (Aug. 1998).

Domb, A.J., "Polyanhydrides. I. Preparation of High Molecular Weight Polyanhydrides", *Journal of Polymer Science: Part A: Polymer Chemistry*, 25, 3373-3386, (1987).

Domb, A.J., "Synthesis and Characterization of Biodegradable Aromatic Anhydride Copolymers", *Macromolecules*, 25, 12-17, (1992).

Dontha, N., "Generation of biotin/avidin/enzyme nanostructures with maskless photolithography", *Analytical Chemistry*, 69(14), 2619-25, (Jul. 15, 1997).

Dukovic, G., "Novel degradable poly(anhydride-esters) for controlled drug release", *The Rutgers Scholar—An Electronic Bulletin of Undergraduate Research*, 1, 1-10, (1999), http://www.scils.rutgers.edu/~weyang/ejournal/volume01/uhriduko/uhriduko.htm.

Erdmann, L., "Polymer Prodrugs with Pharmaceutically Active Degradation Products", *Polymer Preprints*, 38(2), 570-571, (1997).

Erdman et al., "Synthesis and Characterization of a Polymeric Prodrug", *Proceedings of the American Chemical Society Division of Polymeric Materials: Science and Engineering*, 78, Abstract Spring Meeting, Dallas, TX, pp. 194, (Apr. 1998).

Erdmann, L., et al., Chapter 5, "Polymeric Prodrugs: Novel Polymers with Bioactive Components", In: *Tailored Polymeric Materials for Controlled Delivery Systems*, I. McCulloh, et al., (Editors), ACS Symposium Series 709, Developed from a symposium sponsored by the Division of Polymer Chemistry at the 214th National Meeting of the American Chemical Society, Las Vegas, Nevada, Sep. 7-11, 1997, American Chemical Society: Washington, D.C., 83-91, (1998).

Erdmann, L., "Polymeric Prodrugs: Novel Polymers for Delivery of Salicylic Acid", *Annals of Biomedical Engineerinig*, 26 (Suppl. 1), Abstract No. PB.26, Annual Fall Meeting, S-124, (1998).

Erdmann, L., "Polymeric Salicylic Acid: In Vitro and In Vivo Degradation", *Polymer Preprints*, 39(2), 224-225, (1998).

Erdmann, L., "Degradable poly(anhydride ester) implants: effects of localized salicylic acid release on bone", *Biomaterials*, 21(24), 2507-2512, (2000).

Erdmann, L., "Synthesis and degradation characteristics of salicylic acid-derived poly(anhydride-esters)", *Biomaterials*, 21(19), 1941-1946, (Oct. 2000).

Freiberg et al., "Polymer microspheres for controlled drug release", *International Journal of Pharmaceutics*, 282, 1-18 (2004).

Freitas et al., "Microencapsulation by solvent extraction/evaporation: reviewing the state of the art of microsphere preparation process technology", *Journal of Controlled Release*, 102, 313-332 (2005).

Office Action issued by the Japanese Patent Office and English language summary, dispatched Nov. 30, 2010, 9 pages.

Giammona, G., "Polymeric Prodrugs alpha beta poly-hyroxyethyl-dl-aspartamide as macromolecular carrier for some non-steroidal anti-inflammatory agents", *Abstracts from Database BIOSIS Online, Biosciences Information Service*, Philadelphia, PA, Original Publication from the International Journal of Pharmaceutics (Amsterdam), 1 page (1989).

Giammona, G., "Polymeric Prodrugs Alpha Beta Poly-N-hydroxyethyl-DL-aspartamide as a Macromolecular Carrier for Some Non-Steroidal Anti-inflammatory Agents", *International Journal of Pharmaceutics*, 57, 55-62, (1989).

Gouin, S., et al., "New Polyanhydrides Made from a Bile Acid Dimer and Sebacic Acid: Synthesis, Characterization and Degradation", *Macromolecules*, 33, 5379-5383, (2000).

Herbert, C.B., "Micropatterning gradients and controlling surface densities of photoactivatable biomolecules on self-assembled monolayers of oligo(ethylene glycol) alkanethiolates", *Chemistry & Biology*, 4(10), 731-7, (Oct. 1997).

Ibim, S., "Controlled Release Based on Poly(anhydride-co-imides)", *Proc. Intern. Symp. Control. Rel. Bioact. Mater.*, 22, 2 pgs, (1995).

Ibim, S.M., "Poly(anhydride-co-imides): In Vivo Biocompatibility in a rat model", *Biomaterials*, 19(10), 941-951, (1998).

Ibim, S.E., "Preliminary in vivo report on the osteocompatibility of poly(anhydride-co-imides) evaluated in a tibial model.", *Journal of Biomedical Material Research*, 43(4), 374-379, (Winter 1998).

Ito, Y., "Micropatterned immobilization of epidermal growth factor to regulate cell function", *Bioconjugate Chemistry*, 9(2), 277-82, (Mar.-Apr. 1998).

James, C.D., "Patterned Protein Layers on Solid Substrates by Thin Stamp Microcontact Printing", *Langmuir*, 14(4), 741-744, (1998).

Jiang, H.L., "Synthesis, Characterization and In Vitro Degradation of a New Family of Alternate Poly(ester-anhydrides) Based on Aliphatic and Aromatic Diacids", *Biomaterials*, 22(3), 211-218, (2001).

Johnson et al., "Concurrent release of admixed antimicrobials and salicylic acid from salicylate-based poly(anhydride-esters)", *Journal of Biomedical Materials Research*, 91, Part A, 671-678 (2009).

Jucker, M., et al., "Fetal rat septals cells adhere to and extend processes on basement membrane, laminin, and a synthetic peptide from the laminin A chain sequence", *Journal of Neuroscience Research*, 28(4), 507-17, (Apr. 1991).

Kipper et al., "Design of an injectable system based on bioerodible polyanhydride microspheres for sustained drug delivery", *Biomaterials*, 23, 4405-4412 (2002).

Kleinfeld, D., "Controlled outgrowth of dissociated neurons on patterned substrates", *Journal of Neuroscience*, 8(11), 4098-120, (Nov. 1998).

Krogh-Jespersen, E., "Synthesis of a Novel Aromatic Polyanhydride Containing Aminosalicylic Acid", *Polymer Preprints*, 41(1), 1048-1049, (2000).

Langer, R., "New Methods of Drug Delivery", *Science*, 249(4976), 1527-1533, (Sep. 1990).

Laurencin, C.T., "The Bone Biocompatibility of Poly(anhydride-co-imides)—A new generation degradable Polymer for Orthopedic Applications", 41st Annual Meeting of the Orthopedic Research Society, Orlando, FL, 143-24, (1995).

Laurencin, C.T., "Poly(anhydrides-co-imides): In Vivo Biocompatibility Study", *23rd Annual Meeting of the Society for Biomaterials*, New Orleans, LA, 483, (1997).

Laurencin, C.T., "The Biocompatibility of Poly(anhydride-co-imides): High Strength Polymers for Controlled Drug Delivery", *Proc. 24th Int'l Symp. Control. Rel. Bioact. Mater.*, 973-974, (1997).

Laurencin, et al., "The controlled delivery of radiosensitizers: taxol treatment for Ewing Sarcoma", *Proceedings of the 25th Int'l Symp. Control. Rel. Bioact. Mater.*, pp. 236-237, (1998).

Longer, M.A., "Sustained-Release Drug Delivery Systems", *Remington's Pharmaceutical Sciences, 18th Edition, Chapter 91*, 1676-1693, (1990).

Macedo, B., et al., "The in vivo Response to a Bioactive Biodegradable Polymer", *Journal of Dental Research*, 78, Abstract No. 2827, 459, (1999).

Macedo, B., "The In Vivo Response to Bioactive Polyanhydride Monofilament", *Journal of Dental Research*, 79 (Abstract No. 3872), 627, (2000).

Moutziaris et al., "Modulation of the Inflammatory Response for Enhanced Bone Tissue Regeneration", *Tissue Engineering: Part B*, vol. 14, No. 2, 179-186 (2008).

Ouimet et al., "Tunable drug release profiles from salicylate-based poly(anhydride-ester) matrices using small molecule admixtures", *Journal of Bioactive and Compatible Polymers*, 27(6) 540-549 (2012).

Perugini et al., "Sodium Salicylate Inhibitis Proliferation and Induces G1 Cell Cycle Arrest in Human Pancreatic Cancer Cell Lines" *J. Gastrointest Surg.*, 4(1), 24-32, discussion 32-33 (2000).

Pinther, P., "Synthesis of Polyanhydrides Containing Ester Groups", *Die Makromolekulare Chemie, Rapid Communications*, 11(8), 403-408, (Aug. 1990).

Prudencio et al., "Effect of Linker Structure on Salicylic Acid-Derived Poly(anhydride-esters)", *Macromolecules*, 38, 6895-6901 (2005).

Reynolds, et al., "Non-steroidal anti-inflammatory drug (NSAID)-derived poly(anhydride-esters) in bone and periodontal regeneration", *Current Drug Delivery*, 4(3), 233-239 (Jan. 1, 2007).

Rosario-Melendez, et al., "Slow-degrading salicylate-based poly(anhydride-ester) microspheres for undelayed and sustained drug delivery", *PMSE Preprints*, 103-F10, 2 pages (Aug. 2010).

Rosario-Melendez, et al., "Slow-degrading salicylate-based poly(anhydride-ester) microspheres for undelayed and sustained drug delivery", $240^{th}$ *ACS National Meeting & Exposition*, Boston, MA, Aug. 22-26, 2010, poster, 1 page.

Roseborough et al., "Prevention and treatment of excessive dermal scarring", *J Natl Med Assoc*, 96(1), 108-16 (2004).

Rumore et al., "Potential Role of Salicylates in Type 2 Diabetes", *The Annals of Pharmacotherapy*, vol. 44, 1207-1221 (2010).

Schacht, E., "Polymers for Colon Specific Drug Delivery", *Journal of Controlled Release*, 39, 327-338, (1996).

Schmalenberg, K., "Microlithographic patterning of polymer substrates for directed neuronal", *Polymeric Materials Science Engineering, 81, Fall Meeting*, Aug. 22-26, 1999, New Orleans, LA., 97, (1999).

Schmalenberg, K., "Patterned Polymer Substrates for directing Neuronal Growth", *ACS Regional Mid-Atlantic Research Meeting*, (1999).

Schmalenberg, K., "Patterning of polymer substrates for directed neuronal growth studies", *Laboratory for Surface Modification*, (Mar. 18, 1999).

Schmalenberg, K., "Thin Stamp Microcontact Patterned Printing of Protein Layers on Polymer Substrates", *Transactions: Twenty-Fifth Annual Meeting of the Society for Biomaterials*, Apr. 28-May 2, 1999.

Schmeltzer et al., "Optimized Synthesis of Salicylate-based Poly(anhydride-esters)", *Polymer Bulletin*, 49, 441-448 (2008).

Seidel, J.O., "Erosion of Poly(anhydride-co-imides): A Preliminary Mechanistic Study", *J. Appl. Polym. Sci.*, 62(8), 1277-1283, (1996).

Shen, E., "Morphological Characterization of Erodible Polymer Carriers for Drug Release", *Proc. 26th Int'l Symp. Control. Rel. Bioact. Mater.*, 717-718, (1999).

Simon et al., "Dose and Time-Dependent Effects of Cyclooxygenase-2 Inhibition on Fracture-Healing", *The Journal of Bone & Joint Surgery*, vol. 89-A, No. 3, 500-511 (2007).

Spargo, B.J., et al., "Spatially controlled adhesion, spreading, and differentiation of endothelial cells on self-assembled molecular monolayers", *Proceedings of the National Academy of Science USA*,91(23), 11070-11074, (Nov. 8, 1994).

Spitz et al., "Acetylsalicylic acid and salicylic acid decrease tumor cell viability and glucose metabolism modulating 6-phosphofructo-1-kinase structure and activity", *Biochemical Pharmacology*, 77, 46-53 (2009).

St. John, P.M., "Diffraction-based cell detection using a microcontact printed antibody grating", *Analytical Chemistry*, 70(6), 1108-11, (Mar. 15, 1998).

Tang et al., "Controlled delivery of aspirin: Effect of aspirin on polymer degradation and in vitro release from PLGA based phase sensitive systems", *International Journal of Pharmaceutics 357*, 119-125 (2008).

Tashiro, K., et al., "A synthetic peptide containing the IKVAV sequence from the A chain of laminin mediates cell attachment, migration, and neurite outgrowth", *Journal of Biological Chemistry*, 264(27), 16174-82, (Sep. 25, 1989).

Uhrich, K.E., "Synthesis and Characterization of poly(anhydride co-imides): Solution Polycondensation of Biodegradable Polymers Derived from Amino Acids", *Proc. of the American Chemical Society, Division of Polymeric Materials: Science and Engineering*, 70, Spring Meeting, San Diego, CA, 239-240, (1994).

Uhrich, K.E., "Synthesis and Characterization of Degradable poly(anhydride-co-imides)", *Macromolecules*, 28(7), 2184-2193, (1995).

Uhrich, K.E., "Degradation of poly(anhydride-co-imides): Novel Polymers for Orthopedic Applications", *Mat. Res. Soc. Symp. Proc.*, 394, 41-46, (1995).

Uhrich, K.E., "In Vitro Degradation Characteristics of Poly(anhydride-imides) Containing Pyromellitylimidoalanine", *J. Appl. Polymer Sci., Part A, Polym. Chem.*, 34(7), 1261-1269, (1996).

Uhrich, K.E., "In Vitro Degradation Characteristics of Poly(anhydride-imides) Containing trimellitylimidoglycine", *J. Appl. Polymer. Sci.*, 63(11), 1401-1411, (1997).

Uhrich, K.E., "Chemical Changes during in vivo degradation of poly(anhydride-imide) matrices", *Biomaterials*, 19(22), 2045-2050, (1998).

Uhrich et al., "Polymeric Systems for Controlled Drug Release" *Chem. Rev.*, 99, 3181-3198 (1999).

Uhrich, K.E., "Poly(anhydride-ester) Degradation: Mechanical Changes and Correlation to Antibiotic Release", *American Chemical Society, Abstracts of Papers, Part 2*, Abstract No. 121, $221^{st}$ ACS National Meeting, San Diego, CA, Abstract 121, (2001).

Uhrich, K.E., "Synthesis of Aminosalicylate-based polyanhydride Prodrugs: Esters, Amides, and Azos", *American Chemical Society, Abstracts of Papers, Part 2*, Abstract No. 407, 222nd ACS National Meeting, Chicago, IL, Abstract 407, (2001).

Vasir et al., "Bioadhesive microspheres as a controlled drug delivery system", *International Journal of Pharmaceutics*, 255, 13-32 (2003).

Woo et al., "Synthesis and characterization of a novel biodegradable antimicrobial polymer", *Biomaterials*, 21, 1235-1246 (2000).

Woo, G.L., "Biological Characterization of a Novel Biodegradable Antimicrobial Polymer Synthesized with Fluoroquinolones", *J. Biomed. Mater. Res.* 59, 35-45, (2002).

Wu, "Aspirin and Salicylate: An Old Remedy with a New Twist", *Circulation*, 102(17), 2022-3 (2000).

Yamazaki et al., "Aspirin and sodium salicylate inhibit proliferation and induce apoptosis in rheumatoid synovial cells", *Journal of Pharmacy and Pharmacology*, 54, 1675-1679 (2002).

Yazdi et al., "Effects of non-steroidal anti-inflammatory drugs on demineralized bone-induced bone formation", *Journal of Periodontal Research*, 27(1), 28-33, (Jan. 1992).

Yeagy et al, "Characterization and in vitro degradation of salicylate-derived poly(anhydride-ester) microspheres)", *Journal of Microencapsulation*, 23(6), 643-653 (2006).

Yoda, N., "Synthesis of polyanhydrides. XII. Crystalline and high melting polyamidepolyanhydride of methylenebis(p-carboxybhenyl)amide", *Journal of Polymer Science*, 1, 1323-1338, (1963).

Zaugg, R.H., et al., "Modification of Hemoglobin with Analogs of Aspirin", *The Journal of Biological Chemistry*, 255(7), 2816-2821, (1980).

Schmeltzer et al., "Synthesis and Characterization of Salicylic Acid-Based Poly(Anhydride-Ester) Copolymers", *J. Bioact. Compat. Polym.*, 21, 123-133 (2006).

Arredondo et al., Effects of Linkers Substitution on Salicylic Acid-derived Poly(anhydride-esters), website of Rutgers, the State University of New Jersey, 16 pages (2001).

Prudencio, A., "Biodegradable Polyanhydrides for Controlled Drug Release", Dissertation submitted to the Graduate School—New Brunswick, Rutgers, The State University of New Jersey, 228 pages (Oct. 2006).

Prudencio, A., et al., "A Novel Approach for Incorporation of Mono-Functional Bioactive Phenols into Polyanhydrides", *Macromolecular Rapid Communications*, 30, 1101-1108, 2009.

Sparks, et al., "Life after Union: Polymers-R-Us", Presentation at Union College, 40 pages (2007).

Uhrich, K.E., "Designing Polymers for Biomedical Applications", Presentation at Division of Engineering & Applied Science, Harvard University, Cambridge, MA, 50 pages (2002).

\* cited by examiner

*Primary Examiner* — Jason Sims
*Assistant Examiner* — Miriam A Levin
(74) *Attorney, Agent, or Firm* — Viksnins Harris & Padys PLLP

(57) ABSTRACT

The invention provides polymers and methods for their use. Specifically, certain embodiments of the present invention provide a polymer that comprises a plurality of salicylic acid-adipic (SA-Adipic) units of the following formula

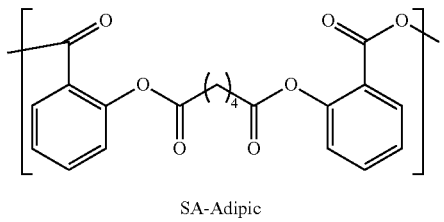

SA-Adipic and a plurality of salicylic acid-diethylmalonic (SA-DEM) units of the following formula

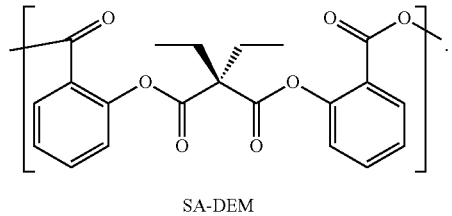

SA-DEM

Certain embodiments of the invention also provide slow degrading microspheres comprising polymers described herein for undelayed and sustained drug delivery. Certain embodiments of the present invention provide methods for treating a chronic eye disease or arthritis in a patient, comprising administering to the patient a therapeutically effective amount of a polymer or microsphere as described herein.

21 Claims, 6 Drawing Sheets

A.

SA-Adipic    SA-DEM

B.

1 = SA-adipic : SA-DEM 25:75
2 = SA-adipic : SA-DEM 50:50
3 = SA-adipic : SA-DEM 75:25

SLOW-DEGRADING POLYMERS COMPRISING SALICYLIC ACID FOR UNDELAYED AND SUSTAINED DRUG DELIVERY

CROSS-REFERENCE TO RELATED APPLICATION(S)

This patent application claims the benefit of priority of U.S. application Ser. No. 61/375,216, filed Aug. 19, 2010, which application is herein incorporated by reference.

STATEMENT OF GOVERNMENT SUPPORT

The invention described herein was made with government support under Grant Number DE 13204 awarded by the NIH. The United States Government has certain rights in the invention.

BACKGROUND

Salicylic acid (SA), the major metabolite of aspirin, has been used for centuries for its analgesic, anti-inflammatory, and antipyretic effects (Wu, Circulation 2000, 102, (17), 2022-3). Recently, SA has been found to be beneficial for many other applications such as wound healing, diabetes, arthritis, and cancer treatment (Roseborough et al., J Natl Med Assoc 2004, 96, (1), 108-16; Rumore et al., Ann Pharmacother 2010, 44, (7-8), 1207-21; Yamazaki et al., J Pharm Pharmacol 2002, 54, (12), 1675-9; Perugini et al., J Gastrointest Surg 2000, 4, (1), 24-32, discussion 32-3; and Spitz et al., Biochem Pharmacol 2009, 77, (1), 46-53). As with all pharmaceutical treatments, best results are obtained when SA is maintained at therapeutic levels in the desired area for as long as it is needed (Uhrich et al., Chem Rev 1999, 99, (11), 3181-98). This presents an issue as oral delivery of SA results in systemic delivery and potential gastrointestinal problems, while not maintaining steady SA concentrations (Amann et al., Eur J Pharmacol 2002, 447, (1), 1-9). Localized delivery from polymers can help overcome these problems while also allowing higher localized SA levels than with systemic delivery.

To better control SA release, salicylic acid-based poly(anhydride-esters) (SA-PAEs) were developed in which SA is chemically incorporated into the polymer backbone via a biocompatible linker molecule. The chemical incorporation of SA enables inherent drug loading capacities up to 90% (w/w), with the capacity to physically admix additional drug to obtain even higher loading (Johnson et al., J Biomed Mater Res A 2009, 91, (3), 671-8). SA-PAEs have been designed to fully degrade over a matter of days to many months. These polymers hydrolytically degrade to exhibit near zero-order SA release after an initial lag period, where minimal to no drug is released. The length of the lag period and the subsequent rate of release can be controlled by changing the linker molecule (Prudencio et al., Macromolecules 2005, 38, (16), 6895-6901).

While the SA-PAE release rate can be changed for different applications, the lag period is should be considered for certain applications. For example, a lag period may be beneficial for applications such as bone regeneration where an initial inflammatory response is desired, but localized reduced inflammation is beneficial at a later time point (Mountziaris et al., Tissue Engineering Part B: Reviews 2008, 14, (2), 179-186; and Simon et al., The Journal of Bone and Joint Surgery 2007, 89, (3), 500-511). On the other hand, the lag period could be considered a disadvantage if SA was desired immediately following implantation, as it would be in applications where inflammation is already present (i.e., arthritis and diabetes).

Accordingly, there is a need for sustained release formulations of SA. In particular, there is a need for sustained release formulations of SA which eliminate the lag period.

SUMMARY OF CERTAIN EMBODIMENTS OF THE INVENTION

Applicant has found slow degrading polymers for undelayed and sustained drug delivery. Certain embodiments of the present invention provide a polymer that comprises a plurality of SA-Adipic units of the following formula

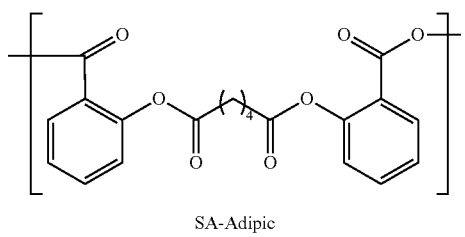

SA-Adipic and a plurality of SA-DEM units of the following formula

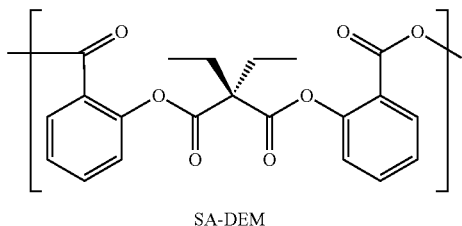

SA-DEM

As used herein, a plurality of SA-Adipic units, means more than one unit of SA-Adipic. In certain embodiments, a plurality of SA-Adipic units is at least about 5 units. In certain embodiments, a plurality of SA-Adipic units is at least about 10 units. In certain embodiments, a plurality of SA-Adipic units is at least about 25 units. In certain embodiments, a plurality of SA-Adipic units is at least about 50 units. In certain embodiments, a plurality of SA-Adipic units is at least about 75 units. In certain embodiments, a plurality of SA-Adipic units is at least about 100 units. In certain embodiments, a plurality of SA-Adipic units is at least about 150 units.

As used herein, a plurality of SA-DEM units means more than one unit of SA-DEM. In certain embodiments, a plurality of SA-DEM units is at least about 5 units. In certain embodiments, a plurality of SA-DEM units is at least about 10 units. In certain embodiments, a plurality of SA-DEM units is at least about 25 units. In certain embodiments, a plurality of SA-DEM units is at least about 50 units. In certain embodiments, a plurality of SA-DEM units is at least about 75 units. In certain embodiments, a plurality of SA-DEM units is at least about 100 units. In certain embodiments, a plurality of SA-DEM units is at least about 150 units.

In certain embodiments, a polymer as described herein and prepared in accordance with the present invention has an average molecular weight of about 20,000 daltons to about 50,000 daltons. In certain embodiments, the average molecular weight is at least about 20,000 daltons. In certain embodiments, the average molecular weight is at least about 25,000 daltons. In certain embodiments, the average molecular weight is at least about 30,000 daltons. In certain embodiments, the average molecular weight is at least about 35,000 daltons. In certain embodiments, the average molecular weight is at least about 40,000 daltons. In certain embodiments, the average molecular weight is at least about 45,000 daltons. In certain embodiments, the average molecular weight is at least about 50,000 daltons.

In certain embodiments, a polymer as described herein and prepared in accordance with the present invention has an average molecular weight of about 10,000 daltons to about 25,000 daltons. In certain embodiments, the average molecular weight is at least about 10,000 daltons. In certain embodiments, the average molecular weight is at least about 15,000 daltons. In certain embodiments, the average molecular weight is at least about 20,000 daltons. In certain embodiments, the average molecular weight is at least about 25,000 daltons.

In certain embodiments, a polymer as described herein and prepared in accordance with the present invention has an average molecular weight of less than about 60,000 daltons. In certain embodiments, the average molecular weight is less than about 50,000 daltons. In certain embodiments, the average molecular weight is less than about 40,000 daltons.

In certain embodiments, the ratio of SA-Adipic units to SA-DEM units in the polymer is about 50:50.

In certain embodiments, the ratio of SA-Adipic units to SA-DEM units in the polymer is about 75:25.

Certain embodiments of the present invention provide a polymer of the following formula:

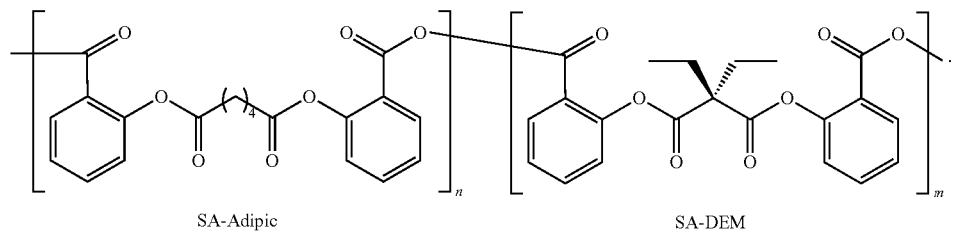

SA-Adipic      SA-DEM

In certain embodiments, "n" is an integer between about 5 and about 75. In certain embodiments, "n" is an integer between about 5 and about 150. In certain embodiments "n" is an integer between about 20 and about 75. In certain embodiments, "m" is an integer between about 5 and about 75. In certain embodiments, "m" is an integer between about 5 and about 150. In certain embodiments "m" is an integer between about 20 and about 75.

Certain embodiments of the present invention provide a pharmaceutical composition comprising a polymer as described herein and a pharmaceutically acceptable carrier.

Certain embodiments of the present invention provide a method for delivering salicylic acid to a patient in need thereof, comprising administering to the patient a therapeutically effective amount of a polymer as described herein.

Certain embodiments of the present invention provide a method for treating a chronic eye disease in a patient, comprising administering to the patient a therapeutically effective amount of a polymer as described herein.

Certain embodiments of the present invention provide a method for treating arthritis in a patient, comprising administering to the patient a therapeutically effective amount of a polymer as described herein. In certain embodiments, the polymer is injected intra-articularly.

Certain embodiments of the present invention provide a polymer as described herein for use in medical treatment or diagnosis.

Certain embodiments of the present invention provide a polymer as described herein for use in therapy.

Certain embodiments of the present invention provide a polymer as described herein for use in treating a chronic eye disease.

Certain embodiments of the present invention provide a polymer as described herein for use in treating arthritis. In certain embodiments, the polymer is injected intra-articularly.

Certain embodiments of the present invention provide a therapeutic method for treating a disease in an animal comprising administering to an animal in need of such therapy, an effective amount of a polymer of the invention.

Certain embodiments of the present invention provide a method of delivering a therapeutically active compound to a host comprising administering to the host a biocompatible and biodegradable polymer of the invention, which degrades into the biologically active compound.

Certain embodiments of the present invention provide a polymer of the invention for use in medical therapy, as well as the use of a polymer of the invention for the manufacture of a medicament useful for the treatment of a disease in a mammal, such as a human.

Certain embodiments of the present invention provide a microsphere comprising a polymer as described herein. In certain embodiments, the polymer has an average molecular weight of about 20,000 daltons to about 50,000 daltons. In certain embodiments, the polymer has an average molecular weight of about 10,000 daltons to about 25,000 daltons. In certain embodiments, the ratio of SA-Adipic units to SA-DEM units in the polymer is about 50:50. In certain embodiments, the ratio of SA-Adipic units to SA-DEM units in the polymer is about 75:25. The polymers as described herein may be processed into microspheres using known methods and procedures commonly employed in the field of synthetic polymers, for example, as described in Example 1. In certain embodiments, the diameter of the microsphere is between about 10 μm to about 30 μm.

Certain embodiments of the present invention provide a pharmaceutical composition comprising a microsphere as described herein and a pharmaceutically acceptable carrier.

Certain embodiments of the present invention provide a method for delivering salicylic acid to a patient in need thereof, comprising administering to the patient a therapeutically effective amount of a microsphere as described herein.

Certain embodiments of the present invention provide a method for treating a chronic eye disease in a patient, comprising administering to the patient a therapeutically effective amount of a microsphere as described herein.

Certain embodiments of the present invention provide a method for treating arthritis in a patient, comprising administering to the patient a therapeutically effective amount of a microsphere as described herein. In certain embodiments, the microsphere is injected intra-articularly.

Certain embodiments of the present invention provide processes and intermediates disclosed herein that are useful for preparing a polymer of the invention and are described herein (e.g. Example 1).

Certain embodiments of the present invention provide polymers and diacids described herein.

DETAILED DESCRIPTION

Figure 1:
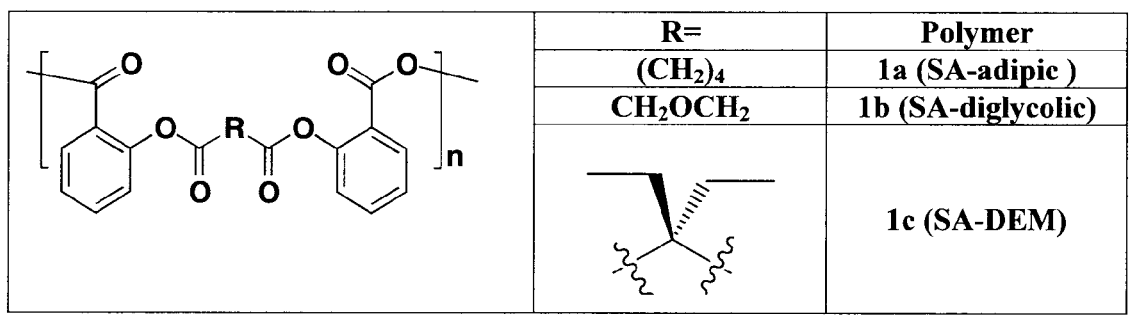
FIG. 1. (A) Structure of moderate-degrading 1a (SA-adipic), fast-degrading 1b (SA-diglycolic), and slow-degrading 1c (SA-diethylmalonic (SA-DEM)) salicylate-based PAEs.

Chemical incorporation of salicylic acid (SA) into the structure of a poly(anhydride-ester) (PAE) allows for a higher percent of drug loading (i.e. 60-90%) (Schmeltzer, R. C. et. al. *Poly. Bull.* 2003, 49, 441) compared to physical incorporation into poly(lactic-co-glycolic acid) (i.e. 20%) (Tang, Y. et. al. *Int. J. Pharm.* 2008, 357, 119). The drug incorporated into the salicylate-based PAE backbone is available as the polymer degrades and SA is released together with the biocompatible "linker molecule" (shown as "R") (Schmeltzer, R. C. et. al. *Poly. Bull.* 2003, 49, 441).

Previous studies using PAE disks have shown that the degradation properties of the polymer can be altered by varying the structure of the "linker molecule". (Prudencio, A. et. al. *Macromol.* 2005, 38, 6895; Carbone, A. L. *Macromol. Rapid Commun.* 2009, 30, 1021). In this work, the goal was to create microspheres (i.e. an injectable drug delivery system) that would release SA in a controlled fashion, at all times for several months for drug delivery applications where long-term release is needed (e.g. to treat chronic eye disease).

Salicylate-based PAEs featuring a diethylmalonic (DEM) linker were successfully formulated into microspheres with smooth surface and narrow size distribution (10-30 μm diameter). The SA release period from the SA-DEM microspheres was significantly longer, compared to SA-adipic microspheres. However, a 10-day lag time in SA release was observed for the slower degrading microspheres.

In an attempt to obtain drug release at all times using the slow degrading microspheres, additives were physically incorporated into the SA-DEM polymer. Surprisingly, the physical incorporation of 10% SA-adipic polymer to the SA-DEM during the formulation gave the best results in terms of approaching the goal to have drug release at all times. One way to overcome the lag time is to formulate copolymers of 50:50 and 75:25 SA-adipic:SA-DEM.

The polymers and microspheres of the invention can be formulated as compositions, e.g., pharmaceutical compositions, and administered to a mammalian host, such as a human patient in a variety of forms adapted to the chosen route of administration, e.g., orally or parenterally, by intravenous, intramuscular, topical or subcutaneous routes.

Thus, the present polymers and microspheres may be systemically administered, e.g., orally, in combination with a pharmaceutically acceptable vehicle such as an inert diluent, excipient or an assimilable edible carrier. They may be enclosed in hard or soft shell gelatin capsules, may be compressed into tablets, or may be incorporated directly with the food of the patient's diet. For oral therapeutic administration, the polymers and microspheres may be combined with one or more excipients and used in the form of ingestible tablets, buccal tablets, troches, capsules, elixirs, suspensions, syrups, wafers, and the like. Such compositions and preparations should contain at least 0.1% of the polymers or microspheres. The percentage of the compositions and preparations may, of course, be varied and may conveniently be between about 2 to about 90% of the weight of a given unit dosage form. The amount of the polymers or microspheres in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a poly(ethylene glycol). Various other materials may be present as coatings or to otherwise modify the physical form of the solid unit dosage form. For instance, tablets, pills, or capsules may be coated with gelatin, wax, shellac or sugar and the like. A syrup or elixir may contain the polymers or microspheres, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the polymers or microspheres may be incorporated into sustained-release preparations, particles, and devices.

The present polymers or microspheres may also be administered intravenously or intramuscularly by infusion or injection. Solutions of the polymer or microspheres can be prepared in water, optionally mixed with a nontoxic surfactant. Dispersions can also be prepared in glycerol, liquid poly (ethylene glycols), triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid poly(ethylene glycols), and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the present polymers or microspheres in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present polymers or microspheres may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, nanoparticles, and the like. Useful liquid carriers include water, alcohols or glycols or water-alcohol/glycol blends, in which the polymers or microspheres can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the polymers or microspheres of the invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the polymers or microspheres of the invention, required for use in treatment will vary with the route of administration, the nature of the condition being treated and the age and condition of the patient and will be ultimately at the discretion of the attendant physician or clinician.

The polymers or microspheres of the invention can be conveniently formulated in unit dosage form. In one embodiment, the invention provides a composition comprising the polymers or microspheres of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Certain embodiments of the invention will now be illustrated by the following non-limiting Example.

Example 1

Polymer microspheres are systems widely used as delivery devices that are used for delivery of drugs, DNA and proteins (Vasir et al., *Int. J. Pharm.* 2003, 255, 13). Microspheres composed of drug molecules physically encapsulated within a biodegradable polymer matrix offer several advantages over other drug delivery devices (Freitas et al., *J. Cont. Rel.* 2005, 102, 313). As the microspheres can be injected into the body, there is no need for their surgical implantation (Kipper et al., *Biomaterials* 2002, 23, 4405). Also, as the microspheres will completely degrade over time, there is no need for their surgical removal (Kipper et al., *Biomaterials* 2002, 23, 4405).

Typically, drug-releasing microspheres are fabricated from polymer systems in which the specific drug molecules are physically incorporated into a polymer matrix (Vasir et al., *Int. J. Pharm.* 2003, 255, 13; Feriberg, et al., *Int. J. Pharm.* 2004, 282, 1; Freitas et al., *J. Cont. Rel.* 2005, 102, 313). However, the microspheres to be described in the following studies are unique in that they are produced from a polymer in which a bioactive compound, namely salicylic acid (SA), is chemically incorporated into the structure of a biodegradable poly(anhydride ester)s (PAEs) (Erdmann et al., *Biomaterials* 2000, 21, 1941; Prudencio et al., *Macromol.* 2005, 38, 6895). This polymeric prodrug allows for a higher percentage of drug loaded in the structure, which will ultimately be available when the polymer degrades (Erdmann et al., *Biomaterials* 2000, 21, 1941).

Previous studies have shown that altering the structural component that binds the SA molecules within the polymer (i.e. the "linker molecule"; shown as "R" in FIG. 1) changes the degradation properties of the resulting polymer (Prudencio et al., *Macromol.* 2005, 38, 6895). For example, using a linear aliphatic linker derived from adipic acid (i.e. an "adipic linker" or polymer 1a) produces a polymer fully degrading in one week (FIG. 1) (Prudencio et al., *Macromol.* 2005, 38, 6895). Using an oxygen-containing aliphatic linker derived from diglycolic acid (polymer 1b) significantly decreases the polymer degradation time to days (FIG. 1) (Carbone, A. L. et al., *Macromol. Rapid Commun.*, 2009, 30, 1021). In further contrast, the use of a branched aliphatic linker derived from diethylmalonic acid (i.e. "diethylmalonic linker" or polymer 1c) significantly increases the polymer degradation time, with only 20% cumulative SA release in three weeks (FIG. 1) (Prudencio et al., *Macromol.* 2005, 38, 6895).

In addition to the decreased SA-release rate of the diethylmalonic-linked polymer, it was found that SA release is not immediate, and that a lag time of 10 days occurs in the degradation profile. As this lag time is undesirable for certain drug delivery applications, methods to shorten and, eventually, eliminate it are needed. Therefore, a series of polymer admixtures were produced by physically mixing polymer 1c with other SA-containing compounds that are expected to produce the necessary immediate release of SA to overcome the observed lag time. The specific admixtures evaluated were as follows: polymer 1c physically mixed with free SA; polymer 1c mixed with its diacid; and polymer 1c mixed with the faster degrading adipic-linked polymer 1a. SA-release from microspheres of these admixtures was monitored for 21 days and was compared to SA-release of microspheres that were solely of polymer 1c.

General Methods

Materials.

All reagents were purchased from Sigma-Aldrich Co. and used without further purification.

Polymer Synthesis.

Figure 2:
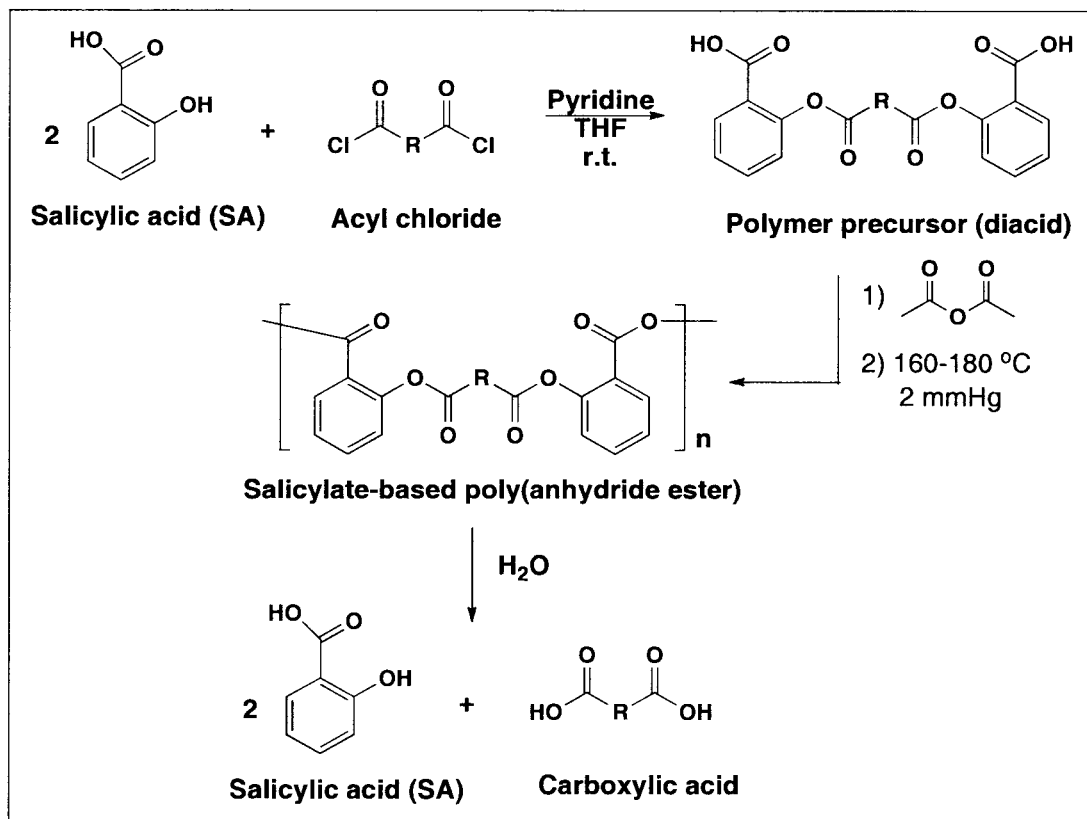
FIG. 2. Synthesis of salicylate-based PAEs. As the polymer degrades, SA is released together with the biocompatible "linker molecule".

Polymers were synthesized and characterized using previously published methods (Prudencio et al., *Macromol.* 2005, 38, 6895; Carbone et al., *Macromol. Rapid Commun.* 2009, 30, 1021). FIG. 2 summarizes the synthesis. Polymer precursors and polymers were characterized using proton nuclear magnetic resonance, infrared spectroscopy, differential scanning calorimetry (to determine melting points and glass transitions temperatures, respectively), and gel permeation chromatography (to determine molecular weight of polymers).

Microsphere Preparation.

Polymers were formulated into microspheres using a modification of previously published oil in water single emulsion solvent evaporation technique (Yeagy et al., *J. Microencap.* 2006, 23, 643). In general, salicylate-based polymer (0.50 g) was dissolved in 3 mL dichloromethane (physical admixtures were prepared by dissolving the polymer together with free SA, diacid or polymer, Table 1) and slowly added to 80 mL of 1% aqueous poly(vinyl alcohol) (PVA) solution at room temperature. The emulsion was homogenized for 2 min using an IKA ultra-turrax T8 homogenizer at speed 3 (approx. 10,000 rpm). The homogenized solution was left stirring for 2 h to allow microsphere formation by solvent evaporation. Microspheres were washed twice with acidic water (pH 1) and isolated by centrifugation at 3,000 rpm for 10 min. They were frozen in a dry ice/acetone bath and lyophilized for 24 h (LABCONO Freeze Dry System/Freezon 4.5 at −40° C. and $133 \times 10^{-3}$ mBar).

TABLE 1

Physical admixtures used.

| | Polymer | Admixture | % Admixture Used |
|---|---|---|---|
| Admixture 2 | SA-DEM (1c) | SA | 10 |
| Admixture 3 | SA-DEM (1c) | SA-DEM Diacid (1c) | 10 |
| Admixture 4 | SA-DEM (1c) | SA-adipic polymer (1a) | 10 |

In Vitro Release Study.

SA release from polymer microspheres was studied at 37° C. in phosphate buffered saline (PBS) at pH 7.4. Microspheres (20.0 mg) were suspended in 20 mL of PBS. Every day, 15 mL of PBS were collected for analysis and replaced with 15 mL of fresh PBS. The amount of SA released was monitored using ultraviolet/visible (UV/vis) spectroscopy. Measurements were taken at 303 nm (wavelength at which SA absorbs and is not overlapped by the absorbance of the linkers) using a Perkin Elmer Lambda XLS spectrophotometer. The data was taken in triplicate and calibrated against SA solutions of known concentrations.

Scanning Electron Microscopy (SEM).

SEM images were taken in an AMRAY-1830I microscope (AMRAY Inc.) after coating the samples with Au/Pd using a sputter coater (SCD 004, Blazers Union Limited).

Results and Discussion

Figure 3:
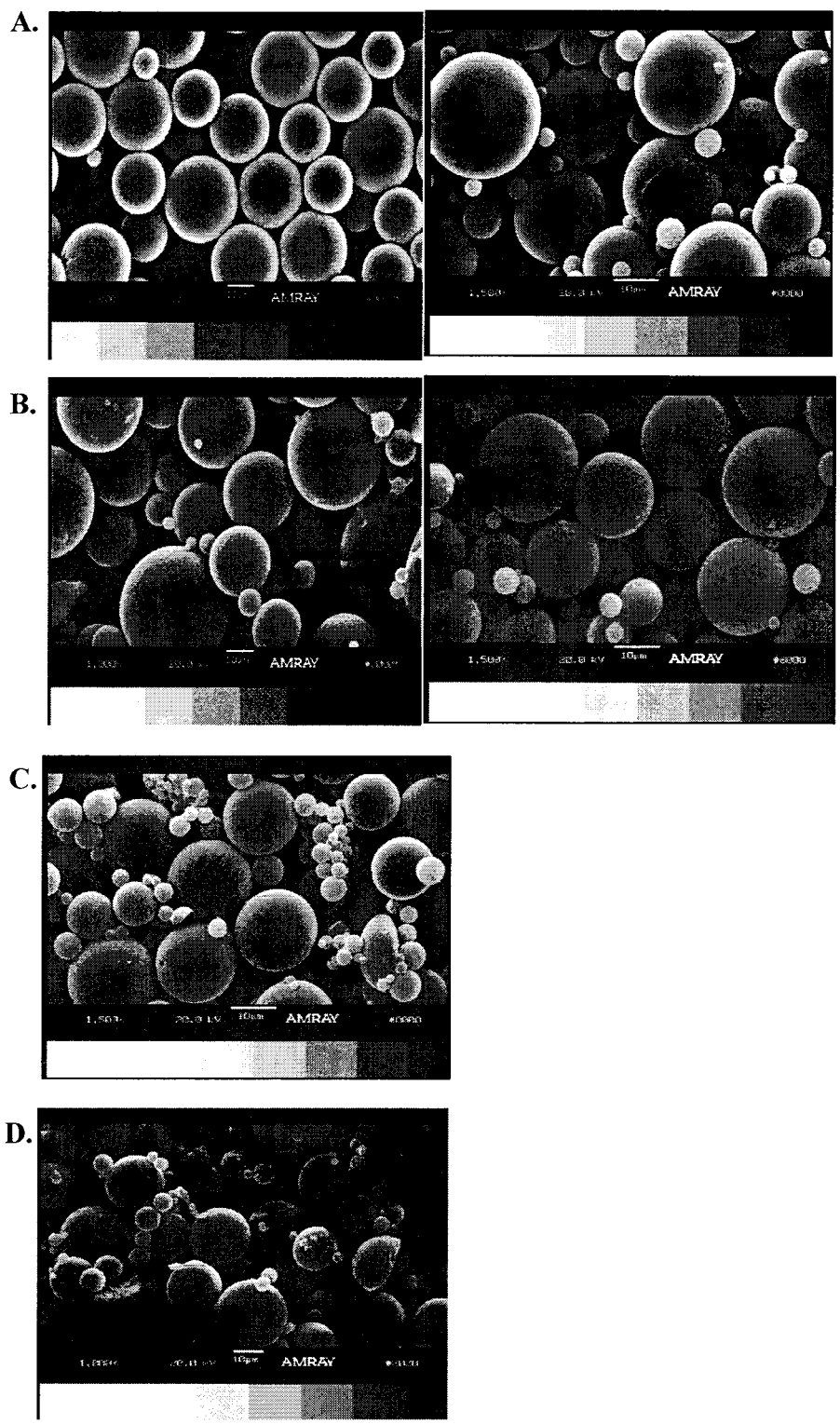
FIG. 3. SEM images of (A) SA-adipic microspheres (i.e. 1a microspheres) at 1000× (left) and 1500× magnification (right) (B) SA-DEM microspheres (i.e. 1c microspheres) at 1000× (left) and 1500× magnification (right) (C) SA-Adipic-co-SA-DEM 50:50 microspheres at 1500× magnification and (D) SA-DEM+10% SA at 1000× magnification.

As shown in FIG. 3, salicylate-based PAEs 1a (FIG. 3a) and 1c (FIG. 3b) were successfully formulated into microspheres. The yields were approximately 85% in both cases. This study documents the first successful fabrication of microspheres from polymer 1c. Scanning electron microscopy (SEM) images were taken to clarify shape, porosity/smoothness, size and size distribution. As shown in FIG. 3, well shaped spherical microparticles with a smooth surface were obtained. These microspheres have a narrow size distribution (10-30 μm diameter), a property that will ensure even degradation/drug release profiles.

In Vitro SA Release: Homopolymers

Figure 4:
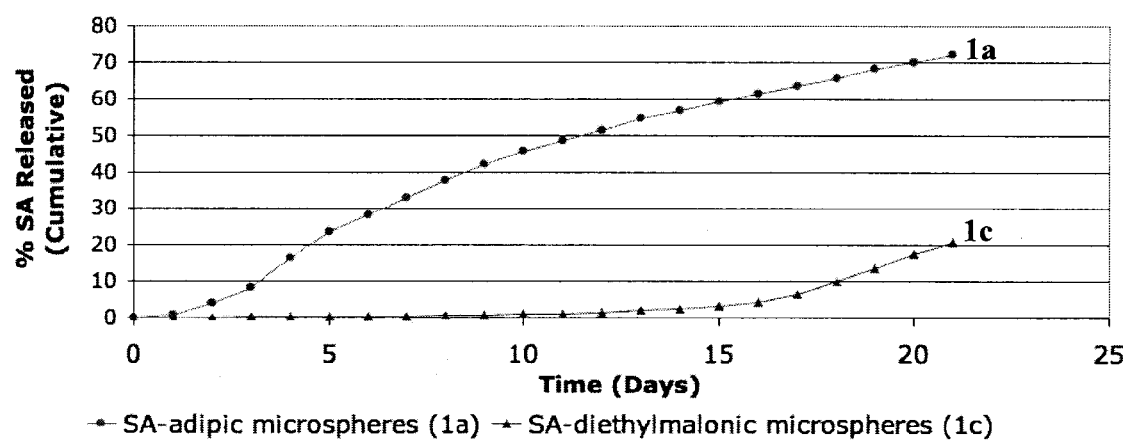
FIG. 4. In vitro hydrolytic degradation profiles of SA-adipic (1a) and SA-DEM (1c) microspheres.

FIG. 4 compares the SA release profile from microspheres of polymer 1a (SA-adipic) and polymer 1c (SE-DEM). As shown, the polymer 1a microspheres released 70% of SA in 21 days. From this data, 100% cumulative release would be expected to occur within a month. In comparison, microspheres of polymer 1c exhibited a significantly slower degradation rate, releasing approximately 20% of SA in 21 days. In addition, a lag time of 10 days (FIG. 4) was observed. The lag time observed in this experiment is consistent with previous accounts (Prudencio, A., et al., *Macromol.* 2005, 38, 6895). For drug delivery applications where drug release is needed at all times, a lag time is not desired.

In Vitro SA Release: Additives

Figure 5:
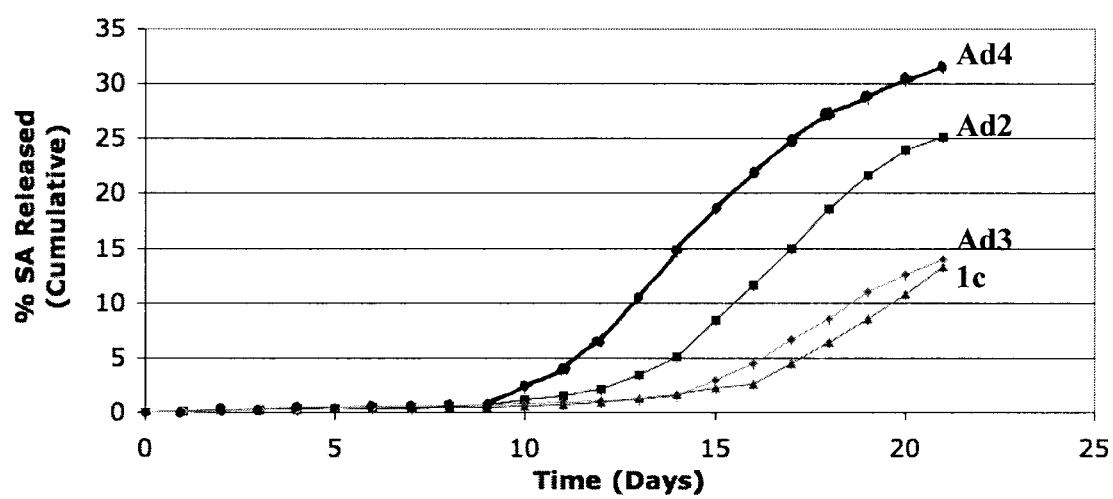
FIG. 5. In vitro hydrolytic degradation profiles of microspheres with physical admixtures.

In an attempt to obtain drug release at all times using the slow degrading microspheres and overcome the lag time, additives (shown in the Table 1) were physically incorporated into the SA-DEM polymer. The release profiles of SA from microspheres of admixtures 2, 3 and 4 were studied. As shown in FIG. 5, none of the admixtures used were successful in overcoming the 10-day lag time previously observed with SA-DEM polymer 1c. This result suggests that the additives within the admixtures were encapsulated by a layer of polymer 1c, that must degrade before the SA-containing additives can be released. Surprisingly, the physical incorporation of 10% SA-adipic polymer to the SA-DEM during the formulation (Admixture 4), gave the best results in terms of approaching the goal to have drug release at all times.

In Vitro SA Release: Copolymers

Figure 6:
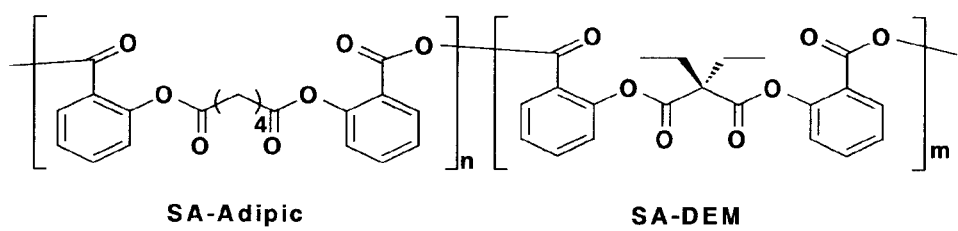
FIG. 6. (A) Structure of SA-adipic:SA-DEM copolymer. (B) In vitro hydrolytic degradation profiles of SA-adipic and SA-DEM copolymer microspheres with varying ratios.
Figure 6:
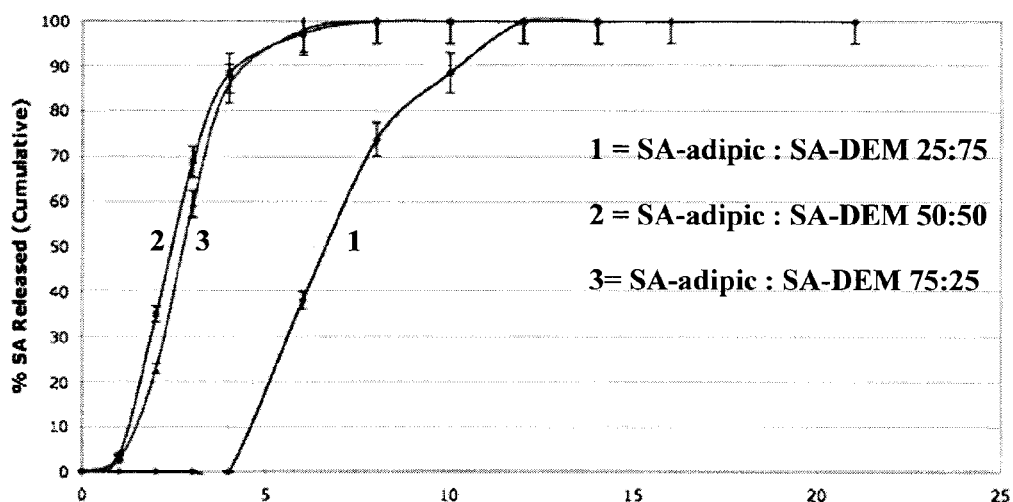

Preliminary results on the degradation of a 50:50 copolymer of SA-adipic:SA-DEM indicated the lag time may be decreased by several days. Accordingly, the effect of combining SA-adipic and the SA-DEM polymers on the SA release profile was investigated by synthesizing random copolymers using different ratios (Table 2 and FIG. 6). The 50:50 and 75:25 (SA-adipic:SA-DEM) ratios overcame the lag time, however the long term release was shortened compared to the SA-DEM.

TABLE 2

| Theoretical Adipic:DEM | Experimental Adipic:DEM | $M_w$Da (PDI) | $T_g$ (° C.) |
|---|---|---|---|
| 100:0 | 100:0 | 14400 (1.9) | 48 |
| 75:25 | 75:25 | 13400 (1.3) | 52 |
| 50:50 | 52:48 | 10400 (1.7) | 43 |
| 25:75 | 29:71 | 11600 (1.2) | 63 |
| 0:100 | 0:100 | 11200 (1.9) | 66 |

CONCLUSION

Salicylate-based PAEs featuring a diethylmalonic-linker were successfully formulated into microspheres with smooth surface and narrow size distribution (10-30 μm diameter). The SA release from these microspheres, as compared to adipic-linked microspheres, was significantly slower. In addition, a 10-day lag time in SA release was observed for the slower degrading microspheres. The best way to overcome the lag time is to formulate copolymers of 50:50 and 75:25 SA-adipic:SA-DEM.

All documents cited herein are incorporated by reference. While certain embodiments of invention are described, and many details have been set forth for purposes of illustration, certain of the details can be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:

1. A polymer that comprises a plurality of salicylic acid-adipic (SA-Adipic) units of the following formula

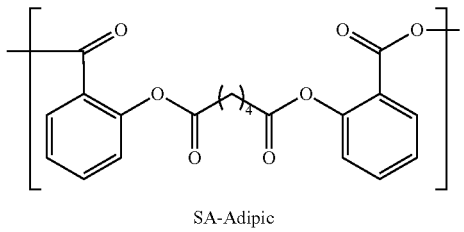

SA-Adipic and a plurality of salicylic acid-diethylmalonic (SA-DEM) units of the following formula

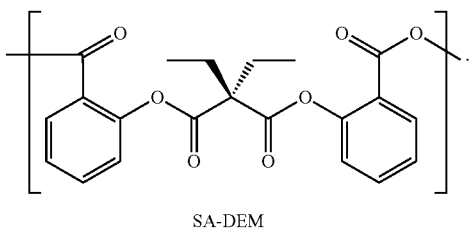

SA-DEM

2. The polymer of claim 1 that has an average molecular weight of about 20,000 daltons to about 50,000 daltons.

3. The polymer of claim 1 that has an average molecular weight of about 10,000 daltons to about 25,000 daltons.

4. The polymer of claim 1, wherein the ratio of SA-Adipic units to SA-DEM units in the polymer is about 50:50.

5. The polymer of claim 1, wherein the ratio of SA-Adipic units to SA-DEM units in the polymer is about 75:25.

6. A pharmaceutical composition comprising a polymer as described in claim 1 and a pharmaceutically acceptable carrier.

7. A method for delivering salicylic acid to a patient in need thereof, comprising administering to the patient a therapeutically effective amount of a polymer as described in claim 1.

8. A method for treating a chronic eye disease in a patient, comprising administering to the patient a therapeutically effective amount of a polymer as described in claim 1.

9. A method for treating arthritis in a patient, comprising administering to the patient a therapeutically effective amount of a polymer as described in claim 1.

10. A microsphere comprising the polymer of claim 1.

11. The microsphere of claim 10, wherein the polymer has an average molecular weight of about 20,000 daltons to about 50,000 daltons.

12. The microsphere of claim 10, wherein the polymer has an average molecular weight of about 10,000 daltons to about 25,000 daltons.

13. The microsphere of claim 10, wherein the ratio of SA-Adipic units to SA-DEM units in the polymer is about 50:50.

14. The microsphere of claim 10, wherein the ratio of SA-Adipic units to SA-DEM units in the polymer is about 75:25.

15. The microsphere of claim 10, wherein the diameter of the microsphere is between about 10 μm to about 30 μm.

16. A pharmaceutical composition comprising a microsphere as described in claim 10 and a pharmaceutically acceptable carrier.

17. A method for delivering salicylic acid to a patient in need thereof, comprising administering to the patient a therapeutically effective amount of a microsphere as described in claim 10.

18. A method for treating a chronic eye disease in a patient, comprising administering to the patient a therapeutically effective amount of a microsphere as described in claim 10.

19. A method for treating arthritis in a patient, comprising administering to the patient a therapeutically effective amount of a microsphere as described in claim 10.

20. The polymer of claim 1, wherein the ratio of SA-Adipic units to SA-DEM units in the polymer is about 25:75.

21. The microsphere of claim 10, wherein the ratio of SA-Adipic units to SA-DEM units in the polymer is about 25:75.

* * * * *

UNITED STATES PATENT AND TRADEMARK OFFICE
CERTIFICATE OF CORRECTION

| | | |
|---|---|---|
| PATENT NO. | : 8,741,317 B2 | Page 1 of 1 |
| APPLICATION NO. | : 13/213843 | |
| DATED | : June 3, 2014 | |
| INVENTOR(S) | : Uhrich et al. | |

It is certified that error appears in the above-identified patent and that said Letters Patent is hereby corrected as shown below:

In the Specification

In Column 1, lines 15-18 under Statement of Government Support:

Replace:

The invention described herein was made with government support under Grant Number DE 13204 awarded by the NIH. The United States Government has certain rights in the invention.

With the following revised paragraph:

This invention was made with government support under DE 13204 awarded by the National Institutes of Health. The government has certain rights in the invention.

Signed and Sealed this
First Day of September, 2015

Michelle K. Lee
*Director of the United States Patent and Trademark Office*

UNITED STATES PATENT AND TRADEMARK OFFICE
CERTIFICATE OF CORRECTION

PATENT NO. : 8,741,317 B2  
APPLICATION NO. : 13/213843  
DATED : June 3, 2014  
INVENTOR(S) : Kathryn E. Uhrich and Roselin Rosario-Meléndez Page 1 of 1

It is certified that error appears in the above-identified patent and that said Letters Patent is hereby corrected as shown below:

In the Specification

Column 1, Lines 15-18 under Statement of Government Support, please delete "This invention was made with government support under DE 13204 awarded by the National Institutes of Health. The government has certain rights in the invention." and insert -- This invention was made with government support under grant numbers DE019923 and DE013207 awarded by the National Institutes of Health. The government has certain rights in the invention. -- therefor.

Signed and Sealed this  
Twenty-seventh Day of December, 2022

Katherine Kelly Vidal  
*Director of the United States Patent and Trademark Office*